(12) United States Patent
Chawla

(10) Patent No.: US 8,201,555 B2
(45) Date of Patent: Jun. 19, 2012

(54) INHALER

(75) Inventor: Brinda Paul Singh Chawla, Nottingham (GB)

(73) Assignee: Brintech International Limited, Nottinghamshire (GB)

( * ) Notice: Subject to any disclaimer, the term of this patent is extended or adjusted under 35 U.S.C. 154(b) by 802 days.

(21) Appl. No.: 12/306,467

(22) PCT Filed: Jun. 26, 2007

(86) PCT No.: PCT/GB2007/050359
§ 371 (c)(1),
(2), (4) Date: Dec. 23, 2008

(87) PCT Pub. No.: WO2008/001132
PCT Pub. Date: Jan. 3, 2008

(65) Prior Publication Data
US 2009/0308388 A1    Dec. 17, 2009

Related U.S. Application Data

(60) Provisional application No. 60/842,858, filed on Sep. 6, 2006.

(30) Foreign Application Priority Data

Jun. 27, 2006  (GB) .................................. 0612693.2

(51) Int. Cl.
*A61M 16/00* (2006.01)
(52) U.S. Cl. .......... 128/203.15; 128/203.19; 128/203.21
(58) Field of Classification Search ............. 128/203.15, 128/203.19, 203.21, 200.14–200.23; 424/46
See application file for complete search history.

(56) References Cited

U.S. PATENT DOCUMENTS

| 4,995,385 A | 2/1991 | Valentini et al. |
|---|---|---|
| 5,152,284 A | 10/1992 | Valentini et al. |
| 6,866,037 B1 * | 3/2005 | Aslin et al. ............... 128/200.23 |
| 7,790,145 B2 * | 9/2010 | Weers et al. .................... 424/46 |
| 2002/0033177 A1 | 3/2002 | Ohki et al. |
| 2005/0016528 A1 * | 1/2005 | Aslin et al. ............... 128/200.23 |

FOREIGN PATENT DOCUMENTS

| GB | 2367756 | 4/2002 |
|---|---|---|
| WO | WO 98/26828 A1 | 6/1998 |
| WO | WO 02/085281 A1 | 10/2002 |
| WO | WO 03/075988 A1 | 9/2003 |
| WO | WO 2005/089483 A1 | 9/2005 |
| WO | WO 2005/089842 A1 | 9/2005 |

OTHER PUBLICATIONS

International Search Report dated Oct. 16, 2007, PCT/GB2007/050359 (5 pages).
Written Opinion dated Oct. 16, 2007, PCT/GB2007/050359 (7 pages).

* cited by examiner

*Primary Examiner* — Glenn Richman
(74) *Attorney, Agent, or Firm* — Glenn M. Massina; Fox Rothschild LLP

(57) ABSTRACT

A dry powder inhaler (101) comprises an inhaler body (110), including an air passageway, and a medicament container (120). The medicament container (120) holds a dose of medicament and is provided with at least one dispensing aperture (123) through which the medicament may be drawn from the medicament container (120). The medicament container (120) is displaceable from a first position, in which the dispensing aperture (123) is occluded, to a second position, in which the dispensing aperture (123) is open and air is able to flow along the air passageway. When the medicament container (120) is in the first position, the air passageway is occluded by the medicament container (120).

31 Claims, 6 Drawing Sheets

INHALER

CROSS-REFERENCE TO RELATED APPLICATION

The present application claims priority under 35 U.S.C. §371 to PCT/GB2007/050359, filed Jun. 26, 2007.

FIELD OF THE INVENTION

This invention relates to an inhaler, ie to a device for the administration of powdered medicament by inhalation.

BACKGROUND OF THE INVENTION

The administration of medicaments by inhalation is well known. Such medicaments are often administered in the form of solid powders. Pressurised metered dose inhalers (MDIs) are one well-known form of administration, but concerns about the environmental effects of the propellants used in such systems have lead to increased attention on so-called dry powder inhalers (DPIs). In such inhalers, a dose of powdered medicament is entrained in a swirling airflow and inhaled, the swirling airflow normally being created by the act of inhalation.

Many DPIs are configured for repeated use, ie for the administration of repeated doses of medicament to a patient. However, for many applications it may be preferable or more convenient for a DPI device to be used only once, for the administration of a single dose of a medicament (or a combination of medicaments), and then to be discarded. In addition to the requirements common to all DPI devices, such as the requirement for the device to deliver the medicament in a form that can reach the intended site of action (eg that a high proportion of the medicament can penetrate deep into the lung, where the medicament is for the treatment of a respiratory condition such as asthma), for disposable devices it is also important that all the medicament should be delivered to the patient, and little or no residue of medicament should remain in the device. Otherwise, disposal of the device could lead to contamination of the environment and the risk that the devices could be subject to abuse. Such a risk may be particularly pertinent in the case of a device that has been used for the administration of a highly potent and/or addictive medicament, or one that is dangerous when not properly used.

U.S. Pat. No. 5,152,284 discloses a disposable inhaler that contains a pre-pierced capsule. The capsule is captivated within an inhaler body formed from at least two parts, and holes in the capsule are closed by a cup that fits around one end of the capsule. The cap can be slid away from the capsule to open the holes. Air can then be drawn through the inhaler body and medicament in the capsule is drawn out through the holes and entrained in the airflow. Such an inhaler suffers from the disadvantage of relative complexity of manufacture, arising from the fact that the inhaler body has to be assembled around the capsule. Also, and particularly importantly, because the holes in the capsule are closed by the slidable cup, they are necessarily located at the end of the capsule that is distal to the mouthpiece. As a result, emptying of the capsule may not be as effective as would be desired, which may result in underdosing and also potentially dangerous medicament residues being discarded with the used inhaler. Also, exhalation through the device would have the effect of dispersing medicament into the surrounding atmosphere.

Another form of inhaler is disclosed in WO-A-03/75988. That document describes an inhaler in which a pre-filled container of medicament is displaced from a first position, in which the container is sealed, to an operative position, in which the container is held stationary within an airway. Certain embodiments of the inhaler are intended to be disposable. In all disclosed embodiments, the medicament container is introduced into a chamber that is considerably larger than the container and the container is immobile within that chamber. It is mentioned that movement of a medicament container, as occurs in other forms of inhaler, eg those disclosed in WO-A-98/26828, may be undesirable as it may be audible.

BRIEF SUMMARY OF THE INVENTION

There has now been devised a form of DPI device which is particularly suitable for the delivery of single doses of medicament, and which overcomes or substantially mitigates disadvantages associated with known forms of inhaler.

According to a first aspect of the invention, there is provided a dry powder inhaler comprising an inhaler body including an air passageway and a medicament container, the medicament container holding a dose of medicament and being provided with at least one dispensing aperture through which the medicament may be drawn from the medicament container, the medicament container being displaceable from a first position, in which the at least one dispensing aperture is occluded, to a second position, in which the at least one dispensing aperture is open and air is able to flow along the air passageway, characterised in that in the first position the air passageway is occluded by the medicament container.

The medicament container may be displaced from the first to the second position by the user pressing directly on the medicament container. Alternatively, the medicament container may form part of an assembly that is slidably mounted within the inhaler body.

Most preferably, in the first position the medicament container is closely received within the air passageway such that the walls of the air passageway occlude the at least one dispensing aperture in the medicament container.

In the second position, the medicament container preferably resides within a dispensing region of the air passageway that is of enlarged dimensions such that air can flow past the medicament container. However, it is strongly preferred that the dispensing region is only slightly greater in dimension than the external dimensions of the container. In particular, it is preferred that the container and the dispensing region should be of similar cross-sectional form, transverse to the direction of airflow past the container, and that the cross-section of the dispensing region should be only slightly greater than that of the container. In particular, the cross-sectional area of the dispensing region is preferably less than 2.0 times the cross-sectional area of the container, and more preferably substantially less than that. For instance, the cross-sectional area of the dispensing region may be less than 1.5 times that of the container, or less than 1.2 times, less than 1.1 times or less than 1.05 times. The dispensing region must have a cross-sectional area that is greater than that of the container, in order to permit air to flow past the container when it is located within the dispensing region, but the cross-sectional area of the dispensing region may be greater than only 1.01 or 1.02 times that of the container, or less. The optimum ratio between the cross-sectional areas of the dispensing region and the container will also depend on the absolute dimensions of the container. Generally, the larger the container, the closer the ratio of the cross-sectional areas will be to 1.0.

It is particularly preferred that the container and the dispensing region should be of similar cross-sectional shape. Most preferably, that shape is circular.

Where, as is preferred, the dispensing region is of only slightly greater dimension than the container, when the medicament container is in the second position there is only a small clearance between the medicament container and the walls of the air passageway. In particular, the clearance may be 2 mm or less, more preferably 1 mm or less, eg in the range 0.05 mm to 1 mm, more preferably 0.1 mm to 0.5 mm. The presence of such a small gap between the medicament container and the surrounding walls of the air passageway offers numerous advantages. In particular, air passing around the medicament container is caused to accelerate, which results in shearing forces being applied to the entrained medicament, thereby breaking up medicament agglomerates and increasing the fine particle fraction of the medicament. The medicament may also be drawn from the medicament container steadily, over a period of time approximating to the full period over which inhalation occurs, rather than being dispensed immediately, as a bolus.

Particularly where, as is preferred, the container and the dispensing region have the same cross-sectional shape, differing only in their dimensions, the flow of air through the narrow gap surrounding the medicament container may also have the effect of centring the medicament container within the dispensing region, such that there is a uniform flow of air around all sides of the container, thus further optimising the dispensing of medicament from the container. It is found that the medicament container empties with little or no residue of the medicament remaining in the medicament container, and that the medicament is dispensed with a high fine particle fraction.

After the medicament container has been displaced from the first to the second position, a flow of air through the device is most commonly generated simply by the act of inhalation by the user. Thus, the user would normally displace the medicament container, place the inhaler to his lips or nostril, and inhale.

For patients who find it difficult or impossible to coordinate inhalation with use of the inhaler, however, a positive airflow may be generated through the inhaler by means such as a bellows or other source of compressed air. In such a way, the inhaler may be used to deliver the medicament to young children, or to elderly or very infirm patients who are unable to inhale in a forceful and coordinated manner.

When the medicament container is displaced into the dispensing region, axial movement of the container along the air passageway is preferably limited by suitable abutments formed within the air passageway. The medicament container is able to move within the dispensing region, but the physical constraints imposed by the close proximity of the walls of the dispensing region and the abutments referred to above mean that movement of the container is severely restricted. Upon initiation of an airflow through the inhaler, either by the user inhaling through the device or by the generation of a positive airflow through the device, the movement of the container may be somewhat chaotic, but generally the container is rapidly drawn into a substantially stationary position, most commonly with a uniform flow of air around all sides of the container. The abutments constitute a seating, into engagement with which the medicament container is drawn. The form and dimensions of the abutments define the size of an air gap between the base of the medicament container and the surrounding surfaces of the dispensing region, and hence the velocity of the air flowing around the medicament container and through the gap. The size of the air gap can thus be optimised for the particular medicament with which the device is being used and/or such factors as the likely inspiratory strength of the user.

In the event that the airflow through the device should be reversed, for instance as a result of the user mistakenly exhaling through the device, the medicament container is displaced back towards the first position, and may then effectively occlude the air passageway, preventing or reducing the release of medicament into the atmosphere.

The inhaler according to the invention is particularly suitable for use as a disposable inhaler, in that it may be pre-loaded with the medicament container, which resides in the first position and is therefore sealed until displaced to the second position. After inhalation, the inhaler may then be discarded. However, the inhaler may also be configured for repeated use. In such embodiments, the air passageway may be capable of being loaded with a medicament container, in the first position, in such a way that the medicament container may be removed from the device after inhalation of the medicament and replaced, immediately or at some subsequent time, by a fresh medicament container.

The device may be manufactured from materials conventionally utilised in inhalation drug delivery devices. For reasons of cost and manufacturing convenience, the device is most preferably manufactured by injection moulding in plastics material. Examples of suitable plastics materials include polycarbonate, polypropylene and polyethylene. Metals may also be used to form all or part of the device. Examples of suitable metals include aluminium and stainless steel. The device may be formed as a single injection-moulded component, or it may comprise a plurality of components that are subsequently bonded or otherwise connected together. An advantage of the use of plastics materials for the inhaler is that transparent materials may be used, enabling visualisation of the medicament container in the dispensing region. If the container too is of transparent material then it becomes possible to verify complete emptying of the container by visual inspection. Injection moulding is also a high precision manufacturing method, and so facilitates production of the inhaler with closely defined dimensions for the air passageway and in particular the air gap between the base of the medicament container and the adjacent surfaces of the dispensing region.

The part of the inhaler body that holds the medicament container in the first position is preferably formed as a rigid plastics component with an opening that is dimensioned to closely receive the medicament container. Any suitable plastics material may be used for this and other rigid components of the inhaler body. Preferred materials include polyolefins, the currently most preferred materials being polypropylene and polycarbonate. The medicament container is preferably received within the opening with an interference fit, such that the container is held securely in place until a user displaces it from the opening by the application of mechanical force. The periphery of the opening may be formed in a flexible material, for example a thermoplastic elastomer, to provide for effective sealing of the opening. This may be achieved using a two-shot moulding process, in which a rigid component, with the opening, is first moulded in a material such as polypropylene and the periphery of the opening is then formed in thermoplastic elastomer in a second moulding step. In other embodiments, the medicament container itself is formed in a relatively soft and slightly deformable material, eg polyethylene, and the component within which it is held, in the first position, is of more rigid material, eg polypropylene or a metal.

The medicament container is preferably of a material that is substantially free of, and impermeable to, moisture. This is in contrast to materials such as gelatine that are conventionally used for pharmaceutical capsules. The container is preferably of plastics material, most preferably polypropylene.

As noted above, the container may be of transparent material. The container may comprise two or more cooperating components that together define the container. Most preferably, the container is formed in two parts that fit together with a snap-fit or the like, one or both parts having formations that define the at least one dispensing aperture at the junction of the two parts. An advantage of such a construction is that the dispensing aperture(s) may be formed at the junction of the two components. This avoids the need for the aperture(s) to be formed in a separate operation during manufacture, eg by piercing. Piercing of, for instance, a conventional gelatine capsule introduces a risk of fragments of capsule material being retained within the capsule and subsequently inhaled. The two or more cooperating parts are preferably manufactured by injection moulding. As an alternative to the use of plastics materials, one or more parts of the container may be formed in metal, eg by pressing from a suitable sheet of metal. Metals that may be used include aluminium. Another advantage of the use of synthetic plastics or metal materials is that such materials are free of any compounds of animal origin, which might be associated with a risk of infection, eg by prion proteins.

The medicament container is most preferably circular in cross-section, and most commonly generally cylindrical, taking the form of a drum. The drum may be relatively squat, having a depth that is of a similar magnitude, or is less than, its diameter. The depth of the container is generally not greater than 2.0 times, and is preferably not greater than 1.5 times, and is more preferably less than, its diameter. The upper and lower faces of the container may be flat or substantially flat or one of the faces may be flat and the other convex or domed in form. The latter arrangement may be particularly advantageous, in that a convex or domed roof of the medicament container facilitates occlusion of the air passageway in the event that the medicament container is urged back towards the second position, eg by the user exhaling into the device (by facilitating engagement of the medicament container with the opening from which it is released when displaced from the first to the second position). Such a convex or domed roof may also facilitate displacement of the medicament container from the first position to the second position.

The medicament container is formed with at least one dispensing aperture through which, when the container is displaced from the first position into the dispensing region of the air passageway, a dose of medicament is dispensed from the container. More preferably, the container is provided with a plurality of dispensing apertures, for example from two to six such apertures.

Preferably the at least one dispensing aperture is formed in the circumference of the medicament container, such that it is sealed by the periphery of the opening in which the medicament container is received when in the first position, and such that it is juxtaposed with the side walls of the dispensing region when in the second position, so that the medicament is drawn from the container directly into the part of the airflow that is travelling at greatest velocity.

Arrangements in which the at least one dispensing aperture is formed in the circumference of the medicament container and in which both the medicament container and the dispensing region are circular in cross-section, the cross-section of the latter being only slightly greater than that of the latter, are particularly advantageous. Thus, according to another aspect of the invention there is provided a dry powder inhaler comprising an inhaler body including an air passageway, and a medicament container engaged with the inhaler body, the medicament container being provided with at least one dispensing aperture formed in the circumference of the container, and the medicament container being displaceable from a first position, in which the at least one dispensing aperture is occluded by engagement with complementary surfaces of the inhaler body, to a second position, in which the medicament container occupies a dispensing region of the air passageway and the at least one dispensing aperture is open, wherein the dispensing region and the medicament container are circular in cross-section and the cross-sectional area of the dispensing region is less than 2.0 times that of the medicament container.

Where, as is preferred, the medicament container has a circular cross-section, a plurality of dispensing apertures are preferably arranged equiangularly around the circumference of the container.

Arrangements in which the medicament container is generally cylindrical and is provided with a plurality of dispensing apertures arranged around the circumference of the container are also particularly advantageous. Thus, according to another aspect of the invention there is provided a dry powder inhaler comprising an inhaler body including an air passageway extending along an axis from an air inlet to an air outlet, and a generally cylindrical medicament container engaged with the inhaler body, the medicament container being provided with a plurality of dispensing apertures spaced apart around the circumference of the container, the medicament container being displaceable inwardly along the axis of the air passageway from a first position, in which the dispensing apertures are occluded by engagement with complementary surfaces of the inhaler body, to a second position, in which the dispensing apertures are open and, in use, medicament may be drawn from the medicament container and entrained in an airflow passing along the air passageway.

The inhaler according to the invention may be used to deliver any medicament that is suitable for administration by inhalation. Examples of such medicaments include those that are suitable for the treatment of asthma, COPD and respiratory infections. Examples of such medicaments are fenoterol, formoterol, pirbuterol, reproterol, rimiterol, salbutamol, salmeterol, terbutaline, isoprenaline, ipratropium bromide, sodium cromoglycate, steroids (eg beclomethasone dipropionate, fluticasone, budesonide, flunisolide, triamcinolone, mometasone and ciclesonide), antivirals, antibiotics and antifungals. The inhaler may be particularly useful for the delivery of vaccines and analgesics, eg the opioid analgesics.

The inhaler may also be used to deliver combinations of two or more different medicaments. Specific combinations of medicaments which may be mentioned include combinations of steroids and $\beta_2$-agonists. Examples of such combinations are beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and salmeterol; ciclesonide and formoterol; mometasone and salmeterol; and mometasone and formoterol. For the delivery of combinations of medicaments, the medicament container may contain a unit dose of the co-formulated combination of medicaments. Alternatively, the container may be partitioned into more than one compartment, each compartment containing one of the combination of medicaments that is to be administered. Examples of medicament containers that may be suitable are described in WO-A-02/085281.

Further medicaments which may be mentioned include systemically active materials, such as, proteinaceous compounds and/or macromolecules, for example, hormones and mediators, such as insulin, human growth hormone, leuprolide and alpha-interferon; growth factors, anticoagulants, immunomodulators, cytokines and nucleic acids.

BRIEF DESCRIPTION OF THE DRAWINGS

Currently preferred embodiments of the invention will now be described in greater detail, by way of illustration only, with reference to the accompanying drawings, in which

FIG. 10 is a sectional side view of a fourth embodiment of an inhaler according to the invention, in a sealed condition, prior to use;

DETAILED DESCRIPTION OF THE INVENTION

Figure 1:
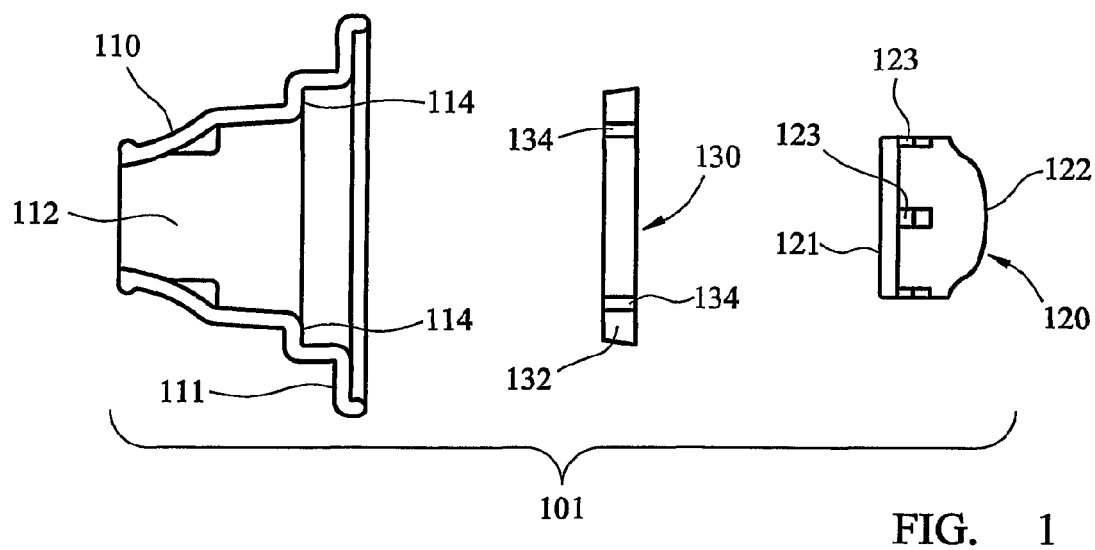
FIG. 1 is an exploded side view, partially in section, of a first embodiment of a disposable unit dose dry powder inhaler according to the invention.

Referring first to FIGS. 1 to 6, a first embodiment of a disposable, unit dose dry powder inhaler according to the invention is generally designated 101. The inhaler 101 comprises three components: a main body 110, a medicament container 120 and a sealing ring 130.

The main body 110 is formed as a unitary component by injection moulding in plastics material. The body 110 comprises an ovoid plate 111 from which a hollow, generally conical or funnel-shaped mouthpiece 112 is upstanding. The mouthpiece 112 is circular in cross-section, the left-hand (as viewed in FIGS. 1 to 3) part of the mouthpiece 112 being tapered to a form that can conveniently be inserted between a user's lips.

The medicament container 120 has the form of a cylindrical drum, the base 121 of which (the left-hand end as viewed in FIG. 1) is flat, and the roof 122 of which (the right-hand end) is domed. A number of apertures 123 are equiangularly spaced around the cylindrical surface of the container 120. In the illustrated embodiment, there are four such apertures 123, spaced at 90° intervals around the container 120. The container 120 is conveniently formed from two components, each of which is injection-moulded in plastics material. The two components are a cup that constitutes the cylindrical wall of the container 120 and the domed roof 122, and a flat plate that engages the open mouth of the cup with a snap or interference fit. The rim of the cup is conveniently formed with slots that constitute the apertures 123 once the flat plate has been engaged with the cup to form the assembled container 120.

The sealing ring 130 comprises a support ring 132 of a relatively rigid plastics material. A seal 134 of an elastomeric material, eg a thermoplastic elastomer, is applied to the inner circumference of the support ring 132. The sealing ring 130 may be produced by a two-shot moulding process, in which the support ring 132 is first moulded and the elastomeric material is then moulded onto the support ring to form the seal 134. In other embodiments, the sealing ring 130 may consist of a single component, formed in a single material that has sufficient rigidity to hold the sealing ring 130 in place but sufficient flexibility to provide an adequate seal.

Figure 2:
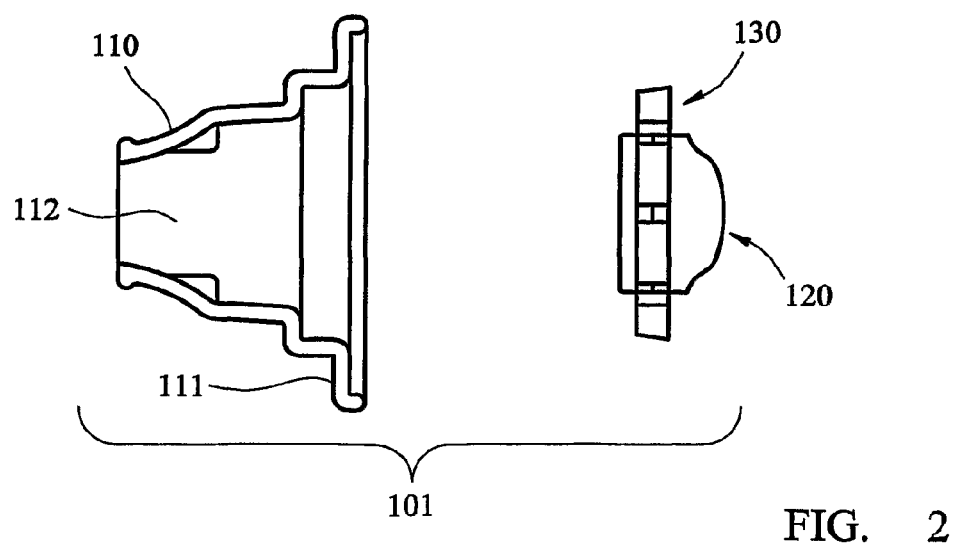
FIG. 2 is a view similar to FIG. 1, but with a unit dose medicament container forming part of the inhaler engaged with a sealing ring.
Figure 3:
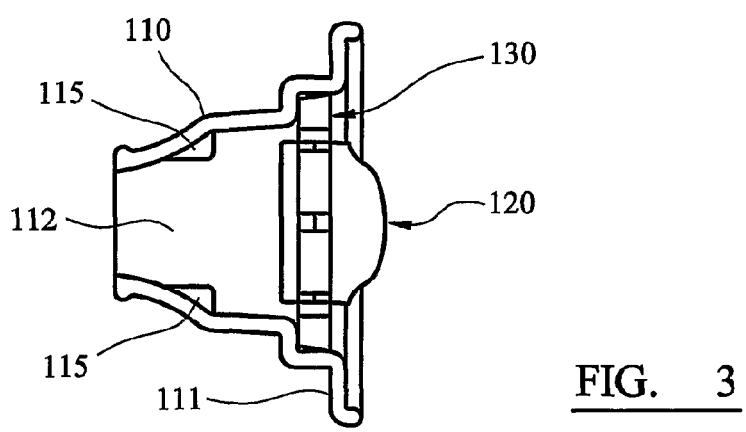
FIG. 3 is a view similar to FIGS. 1 and 2, showing the inhaler in an assembled condition, prior to use.
Figure 4:
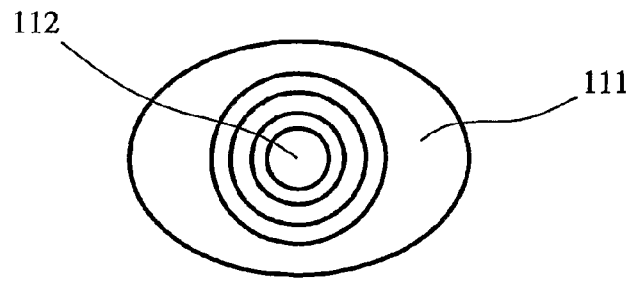
FIG. 4 is a front view of an inhaler body forming part of the inhaler of FIGS. 1 to 3.
Figure 5:
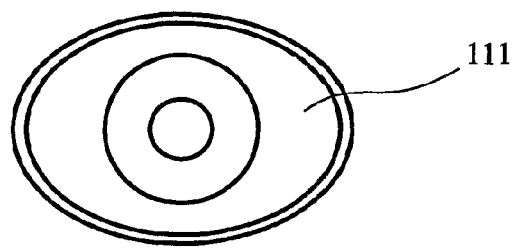
FIG. 5 is a rear view of the inhaler body of FIG. 4.

The sealing ring 130 is dimensioned such that the medicament container 120 can be closely received within the sealing ring 130, such that the seal 134 overlies and closes the apertures 123 in the container 120 (see FIG. 2). Furthermore, the inner surface of the main body 110 is formed with a shoulder 114 that forms a circular recess within which the sealing ring 130 can be received with an interference fit (see FIG. 3).

The medicament container 120 is assembled by filling a unit dose of a powder formulation into the cup that forms part of the container 120. Filling is done with the cup disposed such that its open mouth is uppermost, so that the dose of powder is held in the lower part of the cup (the roof 122 of the container 120). The flat plate that constitutes the base 121 of the container 120 is then engaged with the open mouth of the cup, and the medicament container 120 is pressed into the sealing ring 130, in order to close the apertures 123 in the container 120. Finally, the container 120/sealing ring 130 assembly is pressed into the circular recess in the main body 110 that is defined by the shoulder 114, such that the domed roof 122 of the container 120 projects slightly from the plane of the ovoid plate 112.

Once assembled as described in the preceding paragraph, the inhaler is ready for use. Although the sealing ring 130 effectively closes the apertures 123 in the container 120, preventing egress of medicament powder from within the container 120 and also preventing ingress of moisture into the container 120, for added security the assembled inhaler 101 may be packaged in secondary packaging, for instance a foil sachet.

Figure 6:
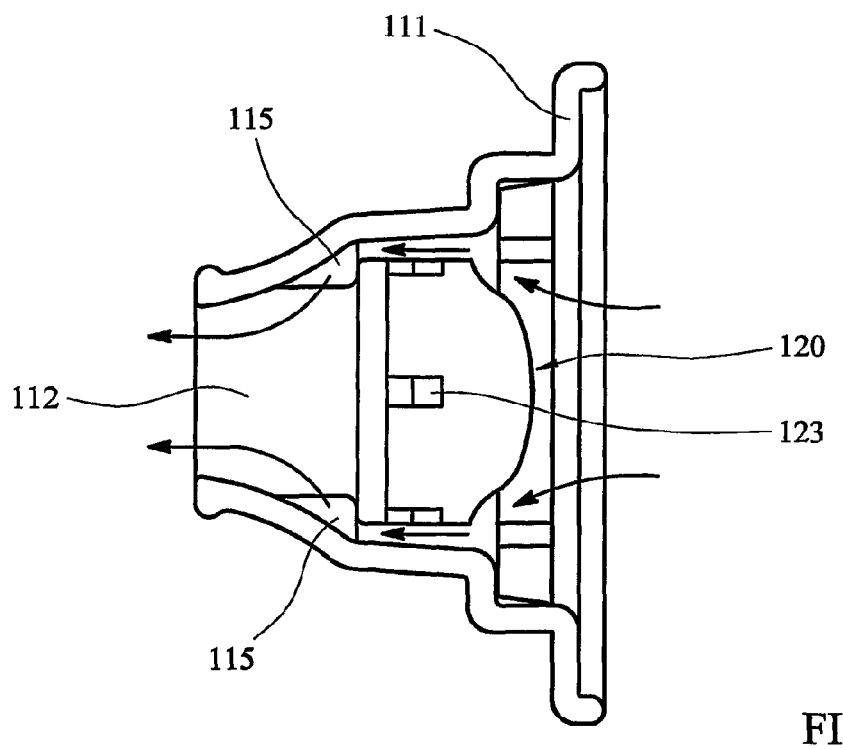
FIG. 6 is a view similar to FIG. 3, but on a slightly enlarged scale, showing the inhaler in an operative condition, during inhalation.

When it is desired to use the inhaler 101 to administer the unit dose of medicament from the container 120, the inhaler 101 is removed from any secondary packaging, and the user then depresses the medicament container 120 into the main body 110, to the position shown in FIG. 6. This is most easily accomplished by the user positioning the inhaler 101 with the mouthpiece 112 between the first two fingers of his dominant hand, and then pressing on the projecting roof 122 of the container 120 using the thumb of the same hand. The container 120 is thus displaced from the sealing ring 30, into the interior of the inhaler body 10. Axial movement of the container 120 into the main body 110 is limited by a plurality of abutments 115 that are formed on the inner surface of the terminal, tapered part of the mouthpiece 12. In the operative configuration shown in FIG. 6, there is a small clearance between the medicament container 120 and the internal walls of the main body 110 that is sufficient for air to flow around the medicament container 120 when the user inhales at the mouthpiece 112. Axial movement of the container 120 is limited by the abutments 115 at one extreme, and abutment with the sealing ring 130 at the other extreme.

Having depressed the medicament container 120 to the position shown in FIG. 6, the user places the mouthpiece 112 to his lips, and inhales. As indicated by the arrows in FIG. 6, air is drawn through the main body 110, entering the device through the opening in the sealing ring 130 from which the container 120 has been displaced. The air flows between the container 120 and the internal walls of the main body 110, and as it does so medicament from within the container 120 is entrained in the airflow and inhaled.

The act of inhalation draws the container 120 away from the sealing ring 130, its axial movement within the main body 110 being limited by contact with the abutments 115. The flow of air around the medicament container 120 acts to centre the medicament container 120 within the main body 110. In the event that the user should blow air into the device, rather than inhale from the device, the medicament container 120 is urged backwards, into contact with the sealing ring 130. This has the beneficial effect of blocking the flow of air through the device, thereby preventing or inhibiting the discharge of medicament into the surrounding atmosphere.

It is found that inhalation by the user effectively empties the medicament powder from the container 120, thereby leading to uniform and reproducible dosing. Also, the small dimensions of the path along which the air flows between the container 120 and the walls of the main body 110 result in strong shearing forces being applied to the entrained medicament, causing break-up of agglomerated particles and increasing the fine particle fraction. Also, the medicament is drawn from the medicament container 120 gradually, rather than as a single bolus, which may lead to improved dosing.

Figure 7:
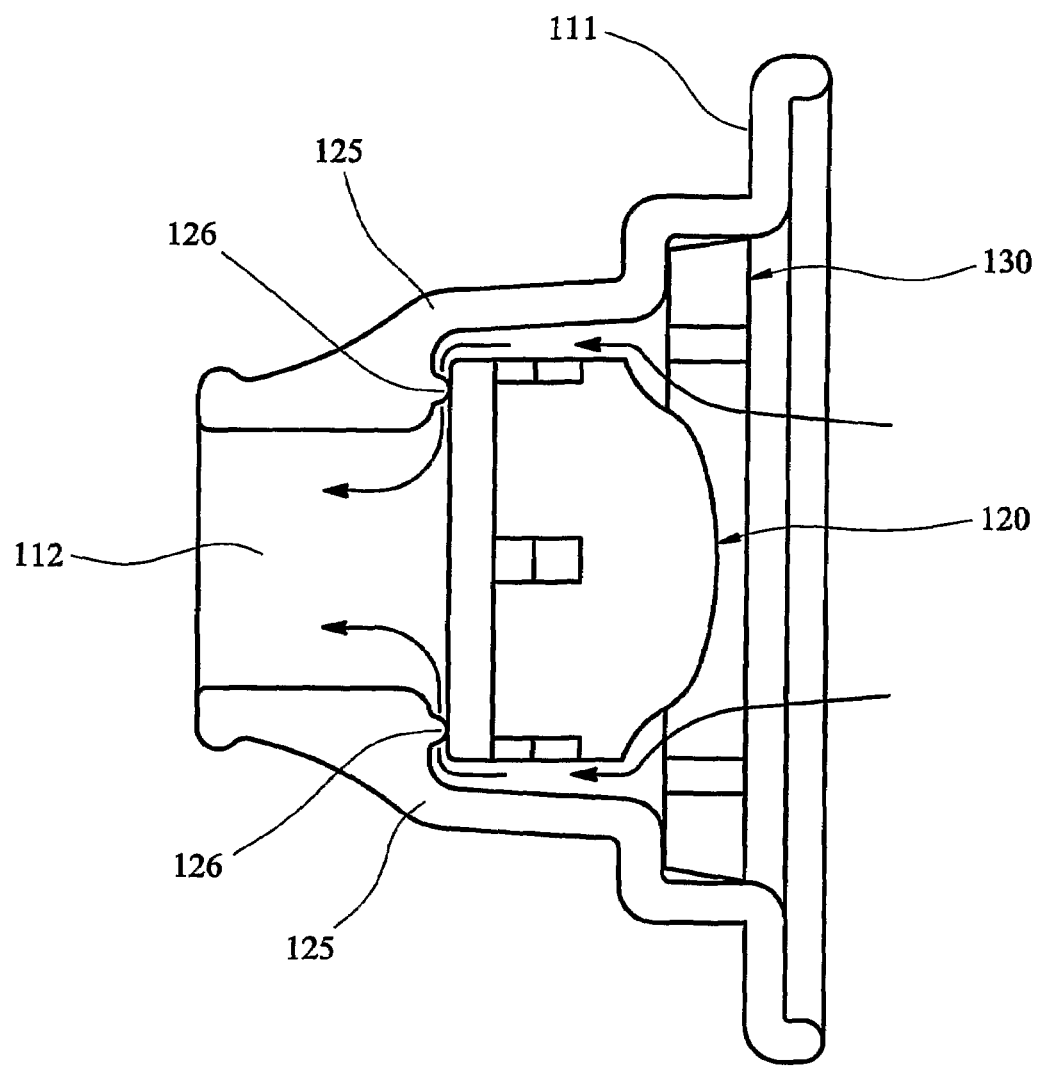
FIG. 7 is a view similar to FIG. 6, showing a second embodiment of an inhaler according to the invention.

The embodiment shown in FIG. 7 is broadly similar to that of FIGS. 1 to 6, and corresponding parts are indicated by the same reference numerals. In the second embodiment, however, the abutments 115 are replaced by a circumferential shoulder 125, from which several small lugs 126 are upstanding. The lugs 126 define a precise separation between the shoulder 125 and the base of the medicament container 120.

Figure 8:
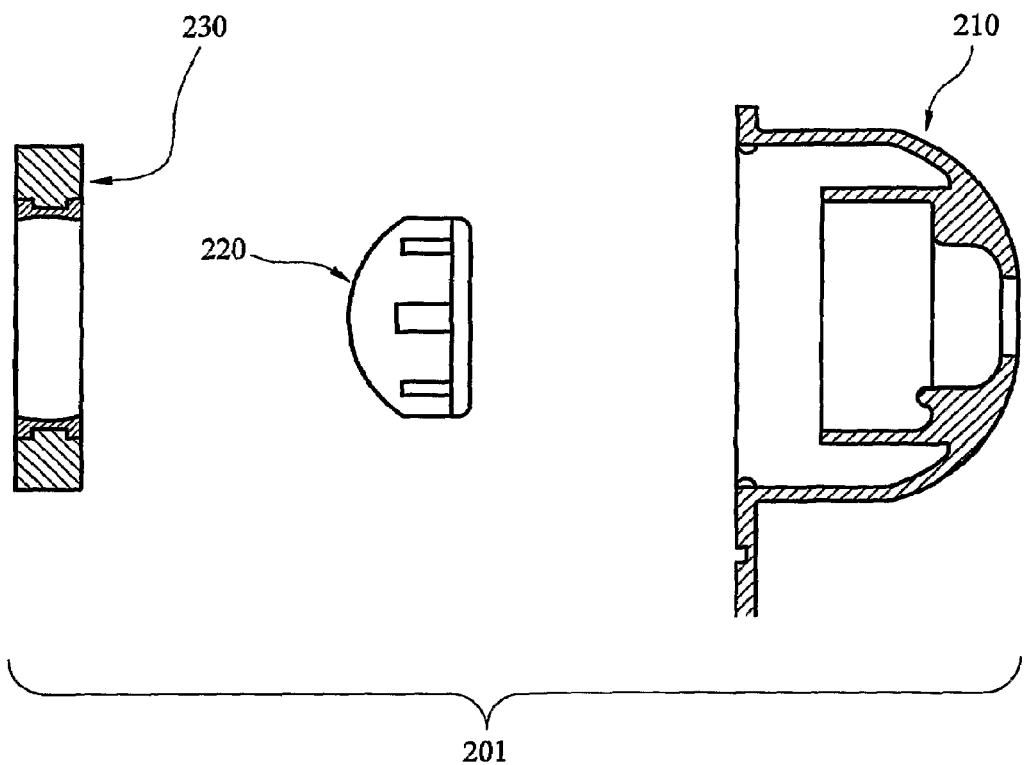
FIG. 8 is a view similar to FIG. 1, but of a third embodiment of an inhaler according to the invention, that is intended for nasal application.
Figure 9:
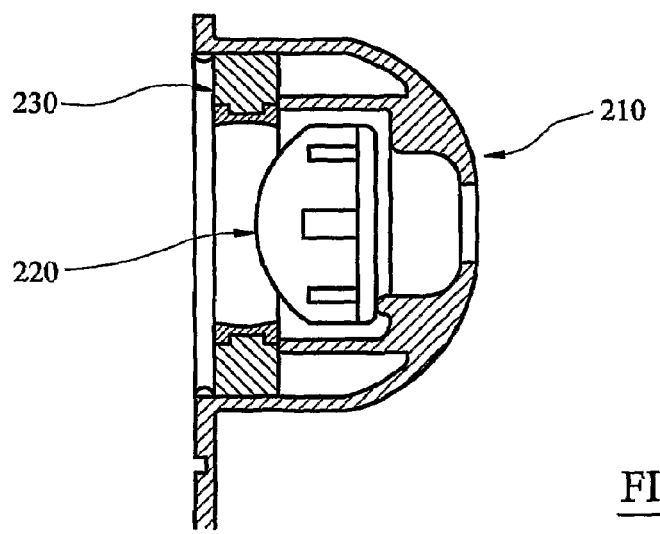
Figure 10:
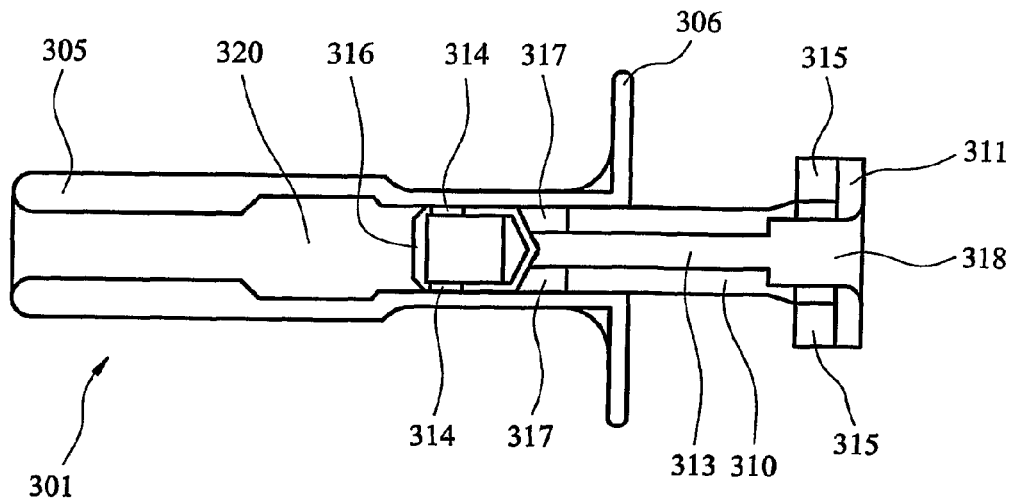
FIG. 10 is a view similar to FIG. 6, showing the inhaler of FIG. 9 in an operative condition.

Turning now to FIGS. 8 and 9, a third embodiment of an inhaler according to the invention is generally designated 201, and is intended for the administration of powdered medicament by nasal inhalation. The inhaler 201 is broadly similar in construction to the first embodiment described above, in that it comprises a main body 210, a medicament container 220 that may in fact be identical to that of the first embodiment, and a sealing ring 230 that may also be identical to that of the first embodiment. The principal difference between the third embodiment 201 and the first 101, is that the main body 210 of the former has a domed, rather than conical or funnel-like, shape. The effect of this is that, when the main body 210 is pressed to the user's nostril, it closes the nostril and so all air that is inhaled passes through the device, rather than some of the air passing around the exterior of the device.

The fourth embodiment of an inhaler according to the invention, generally designated 301, and depicted in FIGS. 10 to 13, is constructed in the form of a syringe. In particular, the inhaler 301 comprises an elongate, tubular body 305, one end of which (the right-hand end, as viewed in the Figures) is formed with an integral flange 306, by which the inhaler 301 can be gripped and operated, as described below.

A plunger 310 is mounted for sliding movement within the tubular body 305. The tip of the plunger 310 is formed with a recess 312, the mouth of which is closed by a closure disc 316 that engages the recess 312 with a snap fit. The recess 312 and the closure disc 316 constitute a medicament container that holds a unit dose of medicament. Dispensing apertures 314 are formed in the medicament container, at the junction of the walls of the recess 312 and the closure disc 316. The external walls of the recess 312 and the closure disc 316 are dimensioned to have a sealing fit with the internal walls of the tubular body 305 so that, when the inhaler 301 is in the condition shown in FIG. 10, the dispensing apertures 314 are completely sealed. In order to ensure a good seal, the tubular body 305 is moulded in a rigid plastics material such as polypropylene, and the plunger 310 and closure plate 316 in a softer, slightly deformable material such as polyethylene.

The plunger 310 has an enlarged head 311 and an internal bore 313. Lateral air inlets 315 in the head 311 permit flow of air through the bore 313 even if the open end of the bore 313 is blocked, eg by the user's thumb. A further set of lateral air passages 317 are provided in the piston 315, immediately above the medicament container.

Figure 11:
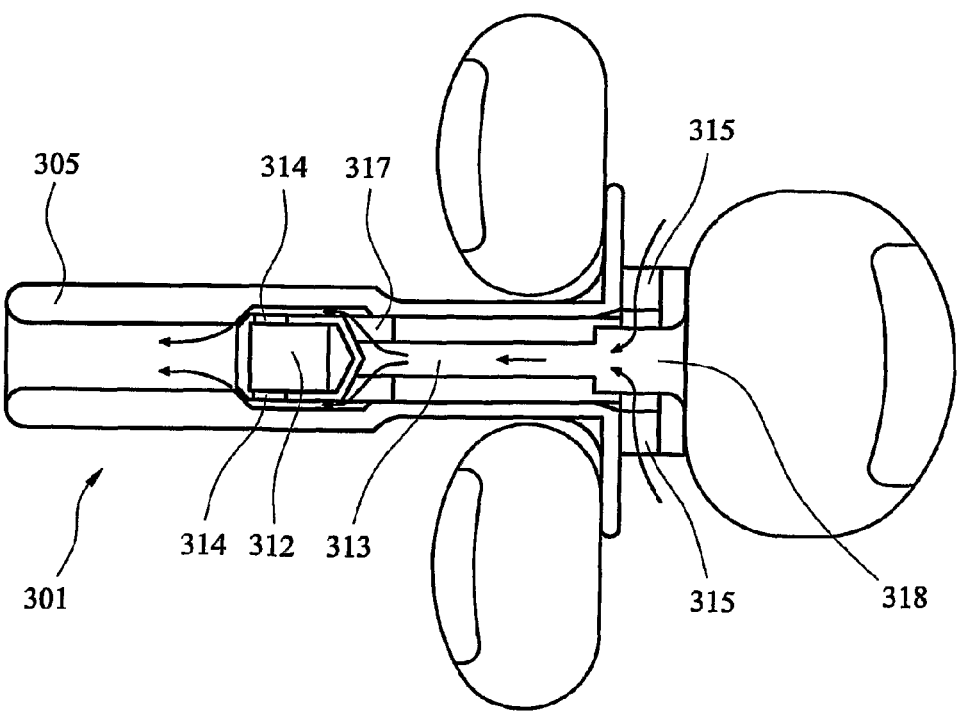
FIG. 11 is a view similar to FIG. 10, showing the inhaler in an operative condition.

A central part 320 of the tubular body 305 is of slightly enlarged dimensions, so that when the plunger 310 is depressed the medicament container resides within that region 320 of enlarged dimensions and air is able to flow along the bore 313 of the plunger 310, through the lateral air passages 317 and past the medicament container. Thus, in use, the user grasps the inhaler 301 by placing the first two fingers of his dominant hand beneath the flange 306 and depresses the plunger 310 by application of force using the thumb of the same hand (FIG. 11). The user then places the open end of the body 305 to his lips and inhales. Air flows through the bore 313 of the plunger 310 and past the medicament container. The effect of this airflow is to entrain the medicament powder from within the medicament container.

Figure 12:
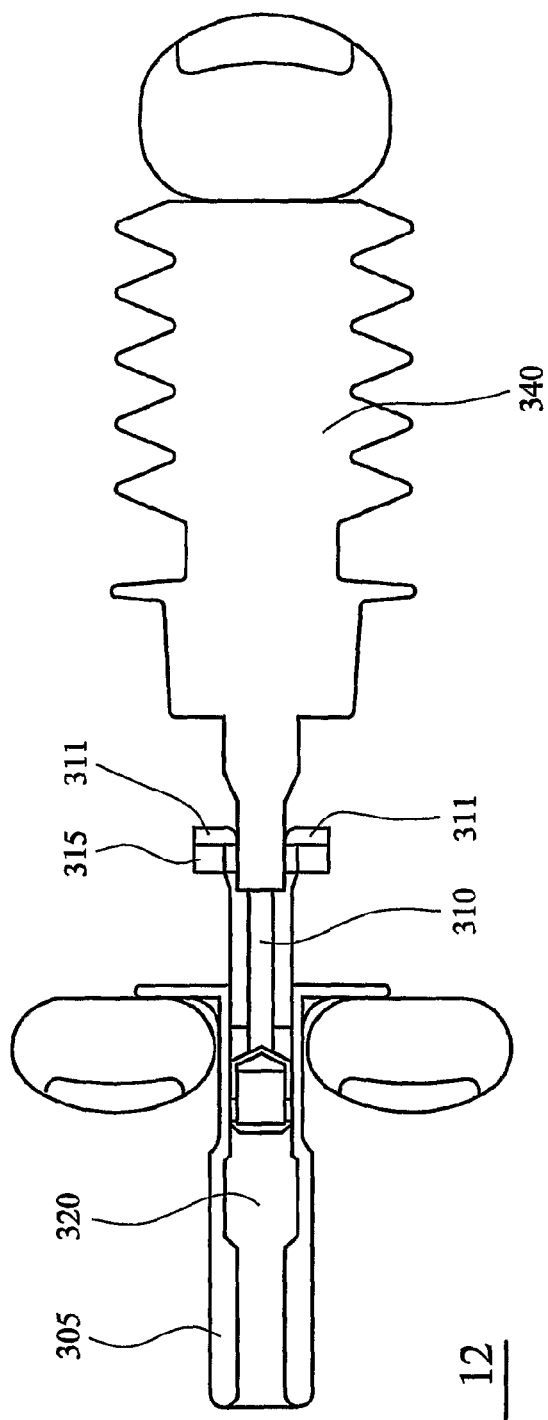
FIG. 12 is a view similar to FIG. 10, wherein a bellows is attached to the inhaler for dispensing of the medicament under positive pressure.
Figure 13:
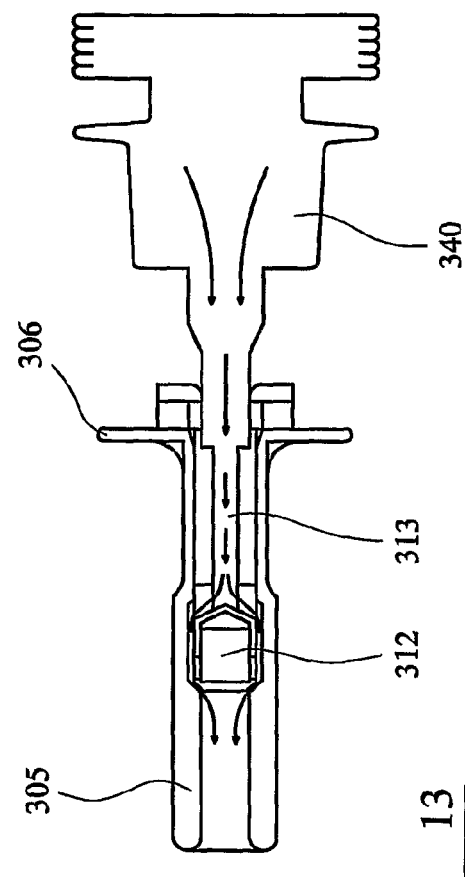
FIG. 13 shows the inhaler in the operative condition, after depression of the bellows to deliver the medicament.

For a patient who is unable to inhale effectively, eg a small child, the inhaler 301 may be used in conjunction with a device for the application of a positive air pressure. Such an arrangement is illustrated in FIGS. 12 and 13. The head 311 of the plunger 310 is formed with a central recess 318 that is dimensioned to receive the tip of a bellows 340 with an interference fit. When the bellows 340 is connected to the plunger 310 in the illustrated fashion, the lateral air inlets 315 in the head 311 are closed.

The plunger 310 is depressed in exactly the same manner as described above in relation to FIGS. 10 and 11, and the device placed to the patient's lips or nostril. Instead of the patient inhaling, however, the medicament is delivered by means of a positive air pressure created by compression of the bellows 340 (as shown in FIG. 13). Zone Name: a1,AMD The inevtion claimed is:

1. A dry powder inhaler comprising an inhaler body including an air passageway and a medicament container, the medicament container holding a dose of medicament and being provided with at least one dispensing aperture through which the medicament may be drawn from the medicament container, the medicament container being displaceable from a first position, in which the at least one dispensing aperture is occluded, to a second position, in which the at least one dispensing aperture is open and air is able to flow along the air passageway, characterised in that in the first position the air passageway is occluded by the medicament container, and wherein, in the second position, the medicament container resides within a dispensing region of the air passageway that is of enlarged dimensions such that air can flow past the medicament container.

2. An inhaler as claimed in claim 1, wherein the medicament container is displaced from the first to the second position by a user pressing directly on the medicament container.

3. An inhaler as claimed in claim 1, wherein the medicament container forms part of an assembly that is slidably mounted within the inhaler body.

4. An inhaler as claimed in claim 1, wherein in the first position the medicament container is closely received within the air passageway such that the walls of the air passageway occlude the at least one dispensing aperture in the medicament container.

5. An inhaler as claimed in claim 1, wherein the container and the dispensing region are of similar cross-sectional form, transverse to the direction of airflow past the container, and the cross-section of the dispensing region is only slightly greater than that of the container.

6. An inhaler as claimed in claim 5, wherein the cross-sectional area of the dispensing region is less than 2.0 times the cross-sectional area of the container.

7. An inhaler as claimed in claim 5, wherein the container and the dispensing region are of circular cross-sectional shape.

8. An inhaler as claimed in claim 1, wherein, when the medicament container is in the second position, the clearance between the medicament container and the walls of the air passageway is 2 mm or less.

9. An inhaler as claimed in claim 8, wherein the clearance is in the range 0.05 mm to 1 mm.

10. An inhaler as claimed in claim 1, wherein in use a flow of air through the device is generated by the act of inhalation by a user.

11. An inhaler as claimed in claim 1, wherein in use a positive airflow is generated through the inhaler by a source of compressed air.

12. An inhaler as claimed in claim 11, wherein the source of compressed air comprises a bellows.

13. An inhaler as claimed in claim 1, which is configured to be a disposable, single-use device.

14. An inhaler as claimed in claim 1, wherein a part of the inhaler body that holds the medicament container in the first position is formed as a rigid plastics component with an opening that is dimensioned to closely receive the medicament container.

15. An inhaler as claimed in claim 14, wherein the periphery of the opening is formed in a flexible material.

16. An inhaler as claimed in claim 15, wherein the flexible material is a thermoplastic elastomer.

17. An inhaler as claimed in claim 1, wherein the medicament container is of plastics material.

18. An inhaler as claimed in claim 1, wherein the medicament container comprises two or more cooperating components.

19. An inhaler as claimed in claim 1, wherein the medicament container is generally cylindrical.

20. An inhaler as claimed in claim 1, wherein the medicament container is provided with a plurality of dispensing apertures.

21. An inhaler as claimed in claim 20, wherein the medicament container is provided with from two to six dispensing apertures.

22. An inhaler as claimed in claim 20, wherein the medicament container is circular in cross-section, and the dispensing apertures are formed in the circumference of the medicament container.

23. An inhaler as claimed in claim 22, wherein the dispensing apertures are arranged equiangularly around the circumference of the container.

24. An inhaler as claimed in claim 23, wherein the medicament container contains a combination of two or more different medicaments.

25. An inhaler as claimed in claim 24, wherein the medicament container contains a unit dose of a co-formulated combination of medicaments.

26. An inhaler as claimed in claim 24, wherein the container is partitioned into more than one compartment, each compartment containing one of the combination of medicaments that is to be administered.

27. An inhaler as claimed in claim 5, wherein the cross-sectional area of the dispensing region is less than 1.05 times the cross-sectional area of the container.

28. An inhaler as claimed in claim 1, wherein, when the medicament container is in the second position, the clearance between the medicament container and the walls of the air passageway is 1 mm or less.

29. An inhaler as claimed in claim 8, wherein the clearance is in the range 0.1 mm to 0.5 mm.

30. A dry powder inhaler comprising an inhaler body including an air passageway, and a medicament container engaged with the inhaler body, the medicament container being provided with at least one dispensing aperture formed in the circumference of the container, and the medicament container being displaceable from a first position, in which the at least one dispensing aperture is occluded by engagement with complementary surfaces of the inhaler body, to a second position, in which the medicament container occupies a dispensing region of the air passageway that is of enlarged dimensions, such that air can flow past the medicament container and the at least one dispensing aperture is open, wherein the dispensing region and the medicament container are circular in cross-section and the cross-sectional area of the dispensing region is less than 2.0 times that of the medicament container.

31. A dry powder inhaler comprising an inhaler body including an air passageway extending along an axis from an air inlet to an air outlet, and a generally cylindrical medicament container engaged with the inhaler body, the medicament container being provided with a plurality of dispensing apertures spaced apart around the circumference of the container, the medicament container being displaceable inwardly along the axis of the air passageway from a first position, in which the dispensing apertures are occluded by engagement with complementary surfaces of the inhaler body, to a second position, in which the medicament container resides within a dispensing region of the air passageway that is of enlarged dimensions, such that the dispensing apertures are open and, in use, medicament may be drawn from the medicament container and entrained in an airflow passing along the air passageway.

* * * * *